United States Patent
Andry

(10) Patent No.: US 10,966,938 B2
(45) Date of Patent: Apr. 6, 2021

(54) COMPOSITION AND METHOD FOR PREVENTING OR TREATING HANGOVER SYMPTOMS

(71) Applicant: JONAND4, LLC, New Orleans, LA (US)

(72) Inventor: Jonathan B. Andry, New Orleans, LA (US)

(*) Notice: Subject to any disclaimer, the term of this patent is extended or adjusted under 35 U.S.C. 154(b) by 22 days.

(21) Appl. No.: 16/734,871

(22) Filed: Jan. 6, 2020

(65) Prior Publication Data

US 2020/0214994 A1 Jul. 9, 2020

Related U.S. Application Data

(60) Provisional application No. 62/788,370, filed on Jan. 4, 2019.

(51) Int. Cl.

| | | |
|---|---|---|
| *A61K 31/05* | (2006.01) | |
| *A61K 36/33* | (2006.01) | |
| *A61K 31/145* | (2006.01) | |
| *A61K 36/28* | (2006.01) | |
| *A61K 31/352* | (2006.01) | |
| *A61K 31/714* | (2006.01) | |
| *A61K 36/67* | (2006.01) | |
| *A61K 31/197* | (2006.01) | |
| *A61K 33/06* | (2006.01) | |
| *A61K 33/00* | (2006.01) | |
| *A61K 31/198* | (2006.01) | |
| *A61K 31/047* | (2006.01) | |
| *A61K 31/185* | (2006.01) | |
| *A61K 36/889* | (2006.01) | |
| *A61P 39/00* | (2006.01) | |

(52) U.S. Cl.
CPC ............ *A61K 31/05* (2013.01); *A61K 31/047* (2013.01); *A61K 31/145* (2013.01); *A61K 31/185* (2013.01); *A61K 31/197* (2013.01); *A61K 31/198* (2013.01); *A61K 31/352* (2013.01); *A61K 31/714* (2013.01); *A61K 33/00* (2013.01); *A61K 33/06* (2013.01); *A61K 36/28* (2013.01); *A61K 36/33* (2013.01); *A61K 36/67* (2013.01); *A61K 36/889* (2013.01); *A61P 39/00* (2018.01)

(58) Field of Classification Search
CPC .... A61K 31/05; A61K 2300/00; A61K 36/33; A61K 31/145; A61K 36/28; A61K 31/352; A61K 31/197; A61K 36/67; A61K 33/06; A61K 33/00; A61K 31/198; A61K 31/047; A61K 31/185; A61K 36/889

See application file for complete search history.

(56) References Cited

U.S. PATENT DOCUMENTS

| | | |
|---|---|---|
| 9,539,295 B2 | 1/2017 | Bohus |
| 9,603,830 B2 | 3/2017 | Powell |
| 9,655,910 B2 | 5/2017 | Kane |
| 2009/0048232 A1 | 2/2009 | Ciccocioppo |
| 2011/0245208 A1 | 10/2011 | Diatchenko |
| 2014/0072662 A1 | 3/2014 | Ciccocioppo |
| 2015/0182455 A1 | 7/2015 | Llamas |
| 2015/0342923 A1* | 12/2015 | Powell ............... A61K 31/198 424/756 |
| 2016/0228385 A1 | 8/2016 | Sievers |
| 2017/0224634 A1 | 8/2017 | Vangara |
| 2018/0125915 A1* | 5/2018 | Mikhail ............... A61K 31/07 |

FOREIGN PATENT DOCUMENTS

| | | |
|---|---|---|
| WO | 2009105507 | 1/2010 |
| WO | 2015140736 | 9/2015 |

OTHER PUBLICATIONS

Hine, et al., Interactions between Cannabidiol and Delta9-THC During Abstinence in Morphine-Dependent Rats, 1975.
Nede, Is the Ultimate Hangover Cure Hidden in Cannabis?, p. 4, 2017.
Liput, et al., Transdermal delivery of cannabidiol attenuates binge alcohol-induced neurodegeneration in a rodent model of an alcohol use disorder, 2013.
Hurd, Cannabidiol: Swinging the Marijuana Pendulum from 'Weed' to Medication to Treat the Opioid Epidemic, pp. 1-2, 2018.

\* cited by examiner

*Primary Examiner* — Kortney L. Klinkel

(57) ABSTRACT

A composition for treating the symptoms of a hangover. The composition is provided in the form of a capsule, pill, liquid, powder for mixing, or patch. The composition includes a therapeutically effective amount of cannabidiol, an antioxidant blend, a detox blend, and a hydration blend. The antioxidant blend includes prickly pear, acai berry extract, and taurine. The detox blend includes milk thistle, dihydromyricetin, glutamine, branched chain amino acids, inositol, and pepper. The hydration blend includes electrolytes, vitamins, and N-acetyl cysteine.

20 Claims, No Drawings

COMPOSITION AND METHOD FOR PREVENTING OR TREATING HANGOVER SYMPTOMS

CROSS-REFERENCE TO RELATED APPLICATION

This application claims the benefit of and priority to U.S. Provisional Patent Application No. 62/788,370, filed on Jan. 4, 2019, which is incorporated herein by reference in its entirety.

BACKGROUND OF THE DISCLOSURE

Hangover is the term used to describe the short-term symptoms experienced by humans after drinking alcohol, also known as ethanol. Hangover symptoms include, but are not limited to, thirst, fatigue, lethargy, headache, dizziness/faintness, loss of appetite, stomach ache, nausea, elevated heart rate, sleep disruption, and biological rhythm disruptions. Other hangover symptoms of which the individual may or may not be aware include, but are not limited to, dehydration, electrolyte imbalance, low blood sugar, vitamin loss, gastrointestinal disturbances, the toxic effects of acetaldehyde and congener, and reduced liver function.

Hangover symptoms are usually experienced the day after drinking. The severity of the symptoms vary depending on the amount and the type of alcohol consumed. A more severe hangover is likely following consumption of a higher volume of alcohol. In fact, the negative effects of alcohol occur even if the individual is unaware of the hangover symptoms.

When abused, alcohol can have a negative effect on a human's brain and body. It is so toxic that the human's liver must work in overdrive to break down the alcohol so it can be expelled from the human's system. The liver needs water to break down alcohol. Because alcohol is a diuretic (i.e., it dehydrates the body), the liver must take water from elsewhere in the body to function, which leads to severe dehydration. The liver takes water from the brain's dura mater, a fluid-filled membrane that separates the brain from the skull. When water is taken from this membrane, it shrinks and causes painful headaches.

Two other less common hangover symptoms are anxiety and depression. When alcohol is consumed, dopamine is released into areas of the brain associated with reward. This is the reason alcohol can be highly addictive to some. The next day, dopamine levels are depleted, which can lead to depression and anxiety.

Alcohol also interferes with the ability to form new long-term memories, leaving intact previously established long-term memories and the ability to keep new information active in memory for brief periods. As the amount of alcohol consumed increases, so does the magnitude of the memory impairments. Large amounts of alcohol, particularly if consumed rapidly, can produce partial (i.e., fragmentary) or complete (i.e., en bloc) blackouts, which are periods of memory loss for events when alcohol was in a person's body.

Hangover remedies have been developed. For example, U.S. Pat. No. 9,603,830 (which is incorporated by reference herein in its entirety) discloses a composition for preventing or treating a hangover that includes dihydromyricetin and N-acetyl cysteine.

Despite the development of hangover remedies, the need still exists for a more effective hangover preventative or treating agent.

SUMMARY OF THE DISCLOSURE

The present disclosure relates to a composition and method for preventing or treating hangover symptoms that includes a therapeutically effective amount of cannabidiol ("CBD") in combination with a therapeutically effective amount of an antioxidant blend, a detox blend, and a hydration blend.

The composition may comprise (i) a therapeutically effective amount of a cannabidiol, (ii) a therapeutically effective amount of an antioxidant blend comprising a mixture of prickly pear, acai berry extract and taurine, (iii) a therapeutically effective amount of a detox blend comprising a mixture of milk thistle, dihydromyricetin, glutamine, branched chain amino acids, inositol, and pepper, and (iv) a therapeutically effective amount of a hydration blend comprising a mixture of electrolytes, vitamins, and N-acetyl cysteine.

In one embodiment, the electrolytes are selected from the group consisting of potassium, magnesium, sodium, chloride, phosphate, and calcium.

In another embodiment, the vitamins are selected from the group consisting of a vitamin B complex, vitamin C, or vitamin D3.

In another embodiment, the amount of cannabidiol in the composition is about 20-40 mg.

In another embodiment, the amount of antioxidant blend in the composition is about 45-90 mg.

In another embodiment, the amount of the detox blend in the composition is about 51-102 mg.

In another embodiment, the amount of the hydration blend in the composition is about 75-150 mg.

In another embodiment, the amount of cannabidiol in the composition is about 20-75 mg.

In another embodiment, the amount of antioxidant blend in the composition is about 45-120 mg.

In another embodiment, the amount of detox blend in the composition is about 50-110 mg.

In another embodiment, the amount of hydration blend in the composition is about 75-200 mg.

The present disclosure also provides a method of preventing or treating hangover symptoms in a human. The method may include administering the composition as described above to the human in the form of a capsule, pill, liquid, a powder for mixing, or a patch.

In one embodiment of the method, the electrolytes are selected from the group consisting of potassium, magnesium, sodium, chloride, phosphate, and calcium.

In another embodiment of the method, the vitamins are selected from the group consisting of a vitamin B complex, vitamin C, or vitamin D3.

In another embodiment of the method, the amount of cannabidiol in the composition is about 20-40 mg.

In another embodiment of the method, the amount of cannabidiol in the composition is about 20-75 mg.

In another embodiment of the method, the amount of antioxidant blend in the composition is about 45-120 mg.

In another embodiment of the method, the amount of the detox blend in the composition is about 50-110 mg.

In another embodiment of the method, the amount of the hydration blend in the composition is about 75-200 mg.

The present disclosure also provides a composition for preventing or treating hangover symptoms consisting essentially of (i) a therapeutically effective amount of a cannabidiol; (ii) a therapeutically effective amount of an antioxidant blend comprising a mixture of prickly pear, acai berry extract, and taurine; (iii) a therapeutically effective amount of an detox blend comprising a mixture of milk thistle, dihydromyricetin, glutamine, branched chain amino acids, inositol, and pepper; and (iv) a therapeutically effective amount of a hydration blend comprising a mixture of potassium, magnesium, calcium, vitamin B12, and N-acetyl cysteine.

DETAILED DESCRIPTION OF THE DISCLOSURE

The present disclosure provides a novel and comprehensive solution to the negative and adverse symptoms of an alcohol-induced hangover. This disclosure contemplates a composition containing a mixture of cannabidiol or CBD and other chemicals, vitamins, and nutrients for treating, ameliorating, and preventing hangover symptoms. As used herein, "alcohol" means ethanol or ethyl alcohol, or any beverage or food containing any percentage of ethanol. As used herein, "symptom" means a physical or physiological effect in a human's body, including effects of which the human is aware and effects of which the human is unaware. As used herein, "hangover" means any physical effect directly or indirectly caused or linked to alcohol consumption, including the consumption of beverages containing ethanol.

The composition contains a therapeutically effective amount of CBD immixed with three specific compositions or blends (e.g. a therapeutically effective amount of (i) an antioxidant composition, (ii) a detox composition, and (iii) a hydration composition) that work conjunctively to relieve and/or ameliorate the causes and symptoms of a hangover. The main or hero ingredient of the composition is CBD, which provides relief from the majority of the hangover's deleterious effects.

The antioxidant blend contains prickly pear, acai berry extract, and taurine. The antioxidant blend contains antioxidants that help to repair damage from the oxidation of ethanol into free radicals, such as acetaldehyde.

The detox blend is a blend of detoxifying agents. The detox blend contains milk thistle, dihydromyricetin (DHM), glutamine, branched chain amino acids (BCAA), inositol, and pepper. The detox blend addresses the toxic effects of alcohol, primarily in the liver and gastrointestinal tract.

The hydration blend contains electrolytes, vitamins, and N-acetyl cysteine. The hydration blend addresses the adverse consequences of the diuretic effects of alcohol metabolism by providing vitamins and substances depleted when alcohol is metabolized. In one embodiment, the electrolytes include one or more of potassium, magnesium, sodium, chloride, phosphate, and calcium. In another embodiment, the vitamins include one or more of a vitamin B complex, vitamin C, and vitamin D3. In a further embodiment, the hydration blend contains potassium, magnesium, calcium, vitamin B12, and NAC.

The composition can be made as a capsule, a pill, a powder for mixing, a liquid (e.g., a liquid shot), or a patch designed to be temporarily affixed to the skin for transdermal migration. The capsule delivery system contains the powder form of each substance. The capsules are to be taken orally with water. The recommended dose is two capsules after drinking alcohol or at the onset of the first hangover symptoms.

One embodiment of the composition of the present disclosure contains the following compounds in the following amounts:

| Compound/Blend | CAS No. | Amount |
| --- | --- | --- |
| CBD | 13956-29-1 | 20 mg |
| Antioxidant Blend: | | |
| Prickly pear | 90082-21-6 | 20 mg |
| Acai Berry Extract | 879496-95-4 | 15 mg |
| Taurine | 107-35-7 | 10 mg |
| Detox Blend: | | |
| Milk Thistle | 84604-20-6 | 20 mg |
| DHM | 27200-12-0 | 10 mg |
| Glutamine | 56-85-9 | 10 mg |
| BCAA | 69430-36-0 | 7 mg |
| Inositol | 87-89-8 | 2 mg |
| Black pepper oil | 8006-82-4 | 2 mg |
| Hydration Blend: | | |
| Potassium | 7440-09-7 | 20 mg |
| Magnesium | 7439-95-4 | 20 mg |
| NAC | 616-91-1 | 5 mg |
| Vitamin B12 | 68-19-9 | 25 mg |
| Calcium | 7440-70-2 | 5 mg |

The composition is formulated by mixing the compounds listed above and encapsulating the composition into capsules. In one embodiment, each capsule contains the listed amount of each compound. Accordingly, the preferred dose of this embodiment of the composition of the present disclosure (i.e., 1-2 capsules) includes: 20-40 mg of a cannabidiol, or any subrange therein, 45-90 mg of the antioxidant blend, or any subrange therein, 51-102 mg of the detox blend, or any subrange therein, and 75-150 mg of the hydration blend, or any subrange therein. More specifically, the preferred dose of this embodiment of the composition of the present disclosure includes: 20-40 mg of a cannabidiol, or any subrange therein, 20-40 mg of prickly pear, or any subrange therein, 15-30 mg of acai berry extract, or any subrange therein, 10-20 mg of taurine, or any subrange therein, 20-40 mg of milk thistle, or any subrange therein, 10-20 mg of DHM, or any subrange therein, 10-20 mg of glutamine, or any subrange therein, 7-14 mg of BCAA, or any subrange therein, 2-4 mg of inositol, or any subrange therein, 2-4 mg of black pepper oil, or any subrange therein, 20-40 mg of potassium, or any subrange therein, 20-40 mg of magnesium, or any subrange therein, 5-10 mg of NAC, or any subrange therein, 25-50 mg of vitamin B12, or any subrange therein, and 5-10 mg of calcium, or any subrange therein.

In another embodiment, the composition of the present disclosure comprises: about 10-11% by weight of cannabidiol, about 23-24% by weight of the antioxidant blend, about 26-27% by weight of the detox blend, and about 39-40% by weight of the hydration blend.

In another embodiment, the composition of the present disclosure comprises: 20-40 mg of a cannabidiol, or any subrange therein, 20-40 mg of prickly pear, or any subrange therein, 15-30 mg of acai berry extract, or any subrange therein, 10-20 mg of taurine, or any subrange therein, 20-40 mg of milk thistle, or any subrange therein, 10-20 mg of DHM, or any subrange therein, 10-20 mg of glutamine, or any subrange therein, 7-14 mg of BCAA, or any subrange therein, 2-4 mg of inositol, or any subrange therein, 2-4 mg of pepper, or any subrange therein, 45-90 mg of electrolytes, or any subrange therein, 5-10 mg of NAC, or any subrange therein, 25-50 mg of vitamins, or any subrange therein.

In yet another embodiment, the composition of the present disclosure comprises: 20-75 mg of a cannabidiol, or any subrange therein, 45-120 mg of the antioxidant blend, or any subrange therein, 50-110 mg of the detox blend, or any subrange therein, and 75-200 mg of the hydration blend, or any subrange therein. This embodiment of the composition of the present disclosure may include: 20-75 mg of a cannabidiol, or any subrange therein, 20-53 mg of prickly pear, or any subrange therein, 15-40 mg of acai berry extract, or any subrange therein, 10-27 mg of taurine, or any subrange therein, 20-43 mg of milk thistle, or any subrange therein, 10-22 mg of DHM, or any subrange therein, 10-22 mg of glutamine, or any subrange therein, 7-15 mg of BCAA, or any subrange therein, 2-4 mg of inositol, or any subrange therein, 2-4 mg of pepper, or any subrange therein, 45-120 mg of electrolytes, or any subrange therein, 5-13 mg of NAC, or any subrange therein, 25-67 mg of vitamins, or any subrange therein.

The synergistic effect between CBD and the other compounds in the present disclosure provides a significant improvement over the state of the art of hangover cures and remedies.

Cannabidiol is a natural analgesic, antiemetic, and neuroprotectant. CBD treats headaches. CBD is not anxiogenic (something that causes anxiety) and can reduce anxiety that is both induced and natural. CBD relieves and ameliorates anxiety, digestive issues, depression, seizures and tremors, inflammation, irritable bowel syndrome, kidney disease, liver disease, migraine headaches, mood disorders, motion sickness, nausea, neurodegeneration, chronic pain, PTSD, sleep disorders and recovery from traumatic brain injuries. CBD is also a powerful antioxidant. As such, CBD addresses common hangover symptoms and causes: dehydration, headaches, nausea and vomiting, fatigue, dizziness, anxiety, depression, and/or lack of concentration. Consuming CBD before alcohol can reduce the amount of alcohol that is absorbed into the blood stream, which prevents some hangover symptoms before they occur.

CBD also exhibits neuroprotective actions, mainly due to its anti-inflammatory and antioxidant properties. CBD reverses alcohol-induced neurotoxicity via a cannabinoid receptor independent antioxidant mechanism.

CBD further substantially limits neuronal damage to hippocampal and entorhinal cortical brain regions that may occur when a large volume of alcohol is consumed. CBD been shown to prevent damage associated with glutamate toxicity in cortical neuron cultures.

The administration of CBD reduces the reinforcing properties, motivation, and relapse for alcohol. CBD is a therapeutic option for the treatment of AUD based on its anxiolytic, antidepressant, antipsychotic, and neuroprotective properties. CBD improves the symptoms of FHF by affecting both brain histopathology and liver function, and thus may serve as therapeutic agent for treating human HE. Cannabinoids are a therapeutic option for treating chemotherapy induced nausea and vomiting.

The benefit of CBD in treating, ameliorating, and preventing hangover symptoms is enhanced by the specific substances contained in the antioxidant blend, the detox, and the hydration blend.

With respect to the antioxidant blend:

Prickly pear, a type of cactus, is an antioxidant that helps to treat hangovers.

Acai berry extract contains chemicals that are antioxidants. Antioxidants protect body cells from the damaging effects of chemical reactions with oxygen (oxidation). Acai has more antioxidant content than cranberry, raspberry, blackberry, strawberry, or blueberry. Chemicals in acai reduce swelling, lower blood sugar levels, and stimulate the immune system.

Taurine is another antioxidant contained in the antioxidant blend.

With respect to the detox blend:

Milk thistle is a natural treatment for liver problems. These liver problems include cirrhosis, jaundice, hepatitis, and gallbladder disorders. Milk thistle is used to treat alcoholic cirrhosis, hepatitis, and drug and alcohol-induced liver damage. Milk thistle treats hangover symptoms and causes by detoxifying and protecting the liver. It boosts the liver's functionality because it brings in lots of antioxidants.

DHM reduces alcohol-induced damage to the liver and brain. Not only does DHM enhance enzymes in the liver responsible for breaking down alcohol and its toxic by-products, but it also reduces the effect alcohol has on GABA receptors in the brain. DHM is a hepatoprotective flavonoid extracted from *Hovenia dulcis*, a Japanese raisin tree. *Hovenia* extracts ameliorate alcohol-induced liver injuries and relieve hangover symptoms, partly by promoting ethanol elimination via enhancement of alcohol dehydrogenase and acetaldehyde dehydrogenase activity.

Glutamine treats and prevents hangover symptoms related to fatigue, stomach irritation, and general sense of illness. Glutamine is an amino acid stored primarily in the muscles and lungs. It is a natural stimulant in abundant supply in the human body, used most often in aiding the immune system and purging excess amounts of ammonia in the body. When alcohol enters the bloodstream, the production of glutamine is inhibited. After alcohol consumption has stopped, the body produces more glutamine than needed (i.e., bonus glutamine). If the person is sleeping, the bonus glutamine stimulates the brain and prevents the person from achieving deep sleep. The effect of the bonus glutamine upon waking is fatigue, often punctuated with tremors, anxiety, and feelings of restlessness. This is known as "glutamine rebound" and can also lead to increased blood pressure, nausea, and a host of other ailments. Glutamine in the composition of the present disclosure calms the body's reaction of glutamine rebound, allowing for deeper sleep and less restlessness and fatigue.

The BCAAs contained in the detox blend are branched chain amino acids: leucine, isoleucine, and valine. These nutrients reduce and treat hangover symptoms.

Inositol is a simple carbohydrate that occurs in animal and plant tissue and is a vitamin of the B group. Inositol, sometimes referred to as vitamin B-8, plays an important part in the health of cell membranes especially in the brain, bone marrow, eyes and intestines. B vitamins are necessary for the proper breakdown and elimination of alcohol in the body.

Black pepper oil boosts serotonin and dopamine levels in the brain. It also reduces alcohol cravings and anxiety.

With respect to the hydration blend:

The composition of the present disclosure contains one or more electrolytes lost during alcohol consumption, including but not limited to potassium, magnesium, phosphate, sodium, chloride, and calcium. The diuretic effect of alcohol depletes these electrolytes and vitamins. The electrolytes are lost in the process of converting alcohol's toxins. The electrolytes are also dispelled in urine. Replenishing these electrolytes speeds up the body's recovery from hangover symptoms. In one embodiment, the electrolytes contained in the hydration blend comprise potassium, magnesium, and calcium.

The composition of the present disclosure also contains one or more vitamins, including but not limited to a vitamin B complex, vitamin C, and vitamin D3. Vitamin B complex is necessary for the proper breakdown and elimination of alcohol in the body. The vitamin B complex is also rapidly depleted from the body due to the diuretic effect of alcohol. Vitamin B complex contained in the hydration blend may include vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), and vitamin B12 (cobalamin). In one embodiment, the vitamins contained in the hydration blend comprise vitamin B12.

N-acetyl cysteine is contained in the hydration blend to aid in the metabolism of alcohol. Humans break down alcohol into acetaldehyde using the enzyme alcohol dehydrogenase. Acetaldehyde is a toxic substance that can cause liver damage and severe hangover symptoms. Dehydrogenase and glutathione are necessary to break down acetaldehyde into a harmless substance. Glutathione is the body's master antioxidant and helps with liver detox and immunity. Humans can only produce a certain amount of glutathione. When glutathione levels are depleted, the body's ability to break down acetaldehyde decreases. N-acetyl cysteine increases the production of glutathione, which is used to break down acetaldehyde, thereby preventing liver damage. In other words, N-acetyl cysteine is a precursor of glutathione and an antioxidant.

Every component of the composition of the present disclosure provides a health benefit regardless of whether the individual has alcohol-induced hangover symptoms. For example, CBD independently provides a plethora of health benefits.

The composition of the present disclosure may comprise any combination of the described compounds and blends. Each method described may include any combination of the described steps in any order, including the absence of certain described steps and combinations of steps used in separate embodiments. Any range of numeric values disclosed herein shall be construed to include any subrange therein.

While preferred embodiments have been described, it is to be understood that the embodiments described are illustrative only and that the scope of the invention is to be defined solely by the appended claims when accorded a full range of equivalents, many variations and modifications naturally occurring to those skilled in the art from a review hereof.

What is claimed is:

1. A composition for preventing or treating hangover symptoms comprising:
    a therapeutically effective amount of a cannabidiol;
    a therapeutically effective amount of an antioxidant blend comprising a mixture of prickly pear, acai berry extract, and taurine;
    a therapeutically effective amount of an detox blend comprising a mixture of milk thistle, dihydromyricetin, glutamine, branched chain amino acids, inositol, and pepper; and
    a therapeutically effective amount of a hydration blend comprising a mixture of electrolytes, vitamins, and N-acetyl cysteine.

2. The composition of claim 1, wherein the electrolytes are selected from the group consisting of potassium, magnesium, sodium, chloride, phosphate, and calcium.

3. The composition of claim 1, wherein the vitamins are selected from the group consisting of a vitamin B complex, vitamin C, or vitamin D3.

4. The composition of claim 1, wherein the amount of cannabidiol in the composition is about 20-40 mg.

5. The composition of claim 4, wherein the amount of antioxidant blend in the composition is about 45-90 mg.

6. The composition of claim 4, wherein the amount of the detox blend in the composition is about 51-102 mg.

7. The composition of claim 4, wherein the amount of the hydration blend in the composition is about 75-150 mg.

8. The composition of claim 1, wherein the amount of cannabidiol in the composition is about 20-75 mg.

9. The composition of claim 8, wherein the amount of antioxidant blend in the composition is about 45-120 mg.

10. The composition of claim 8, wherein the amount of detox blend in the composition is about 50-110 mg.

11. The composition of claim 8, wherein the amount of hydration blend in the composition is about 75-200 mg.

12. A method of preventing or treating hangover symptoms in a human comprising the steps of:
    a) administering the composition of claim 1 to the human in the form of a capsule, pill, liquid, powder for mixing, or patch.

13. The method of claim 12, wherein the electrolytes are selected from the group consisting of potassium, magnesium, sodium, chloride, phosphate, and calcium.

14. The method of claim 12, wherein the vitamins are selected from the group consisting of a vitamin B complex, vitamin C, or vitamin D3.

15. The method of claim 12, wherein the amount of cannabidiol in the composition is about 20-40 mg.

16. The method of claim 12, wherein the amount of cannabidiol in the composition is about 20-75 mg.

17. The method of claim 16, wherein the amount of antioxidant blend in the composition is about 45-120 mg.

18. The method of claim 16, wherein the amount of the detox blend in the composition is about 50-110 mg.

19. The method of claim 16, wherein the amount of the hydration blend in the composition is about 75-200 mg.

20. A composition for preventing or treating hangover symptoms consisting essentially of:
    a therapeutically effective amount of a cannabidiol;
    a therapeutically effective amount of an antioxidant blend comprising a mixture of prickly pear, acai berry extract, and taurine;
    a therapeutically effective amount of an detox blend comprising a mixture of milk thistle, dihydromyricetin, glutamine, branched chain amino acids, inositol, and pepper; and
    a therapeutically effective amount of a hydration blend comprising a mixture of potassium, magnesium, calcium, vitamin B12, and N-acetyl cysteine.

* * * * *